United States Patent [19]

Grandjean et al.

[11] Patent Number: 5,031,621
[45] Date of Patent: Jul. 16, 1991

[54] NERVE ELECTRODE WITH BIOLOGICAL SUBSTRATE

[76] Inventors: Pierre A. Grandjean, Rue Du Mari 7, Bassenge, Belgium; Philip H. J. Lee, 6461 Crackleberry Trail, Woodbury, Minn. 55125

[21] Appl. No.: 446,865

[22] Filed: Dec. 6, 1989

[51] Int. Cl.⁵ .......................... A61B 5/04; A61N 1/05
[52] U.S. Cl. ..................... 128/642; 128/784; 128/419 C
[58] Field of Search ............ 128/642, 784–786, 128/419 C

[56] References Cited

U.S. PATENT DOCUMENTS

| | | | |
|---|---|---|---|
| 3,421,511 | 1/1969 | Schwartz et al. | 128/784 |
| 3,654,933 | 4/1972 | Hagfors | 128/784 |
| 3,774,618 | 11/1973 | Avery | 128/784 |
| 4,258,724 | 3/1981 | Balat | 128/785 |
| 4,341,221 | 7/1982 | Testerman | 128/642 |
| 4,628,944 | 12/1986 | MacGregor et al. | 128/785 |
| 4,852,573 | 8/1989 | Kennedy | 128/642 |
| 4,928,689 | 5/1990 | Hauser | 128/786 X |
| 4,940,065 | 7/1990 | Tanagho et al. | 128/784 |

Primary Examiner—Lee S. Cohen
Attorney, Agent, or Firm—John L. Rooney

[57] ABSTRACT

An electrode and method of making same characterized by a biological material used as a substrate. The electrode is used primarily as a stimulation electrode, but could also be used to monitor electrical activity of neural tissues. The biological substrate is a chronically implantable material of treaterd human or animal tissue. The use of this material tends to prevent undue fibrosis and necrosis of the nerve tissue. An inner layer of a non-biologic dielectric may be used to increase to resistivity of the structure. Similarly an inner layer of shielding material may also be used.

5 Claims, 4 Drawing Sheets

NERVE ELECTRODE WITH BIOLOGICAL SUBSTRATE

BACKGROUND OF THE INVENTION

1. Field of the Invention

The present invention relates generally to electrode systems for stimulation or monitoring electrical activity in nerve tissue and more particularly relates to chronically implantable electrodes.

2. Description of the Prior Art

The use of electrodes to monitor electrical activity and stimulate body tissue is quite old. R. H. Wappler U.S. Pat. No. 1,662,446 teaches an early electrode system. The Wappler electrode is used for acute stimulation only, and is not implantable.

An early stimulation electrode which is chronically implantable is taught by S. I Schwartz, et al. in U.S. Pat. No. 3,421,511. Hagfors U.S. Pat. No. 3,654,933 teaches an improved stimulation electrode for chronic implantation.

Testerman U.S. Pat. No. 4,341,221 teaches an improved electrode for chronic implantation. The Testerman electrode is suitable for monitoring electrical activity in nerve tissue. This electrode uses a substrate of silicone rubber or other material which is inert when chronically implanted. However, as with the other electrodes, the Testerman electrode does not prevent excess fibrotic growth.

SUMMARY OF THE INVENTION

The present invention produces a chronically implantable electrode suitable for stimulation or monitoring of electrical activity in nerve tissue This electrode uses a substrate of biological tissue which has been properly treated to ensure long term resistance to excess fibrotic growth. An electrically conductive surface is fixedly attached to one side of the substrate. This side becomes the inside as the flexible substrate is wrapped about the nerve to be monitored. The resistivity of the biological tissue is used to electrically insulate the exposed nerve tissue and electrically conductive surface in contact therewith. An electrically insulated conductor couples the electrically conductive surface with electronic circuitry.

For those applications requiring greater resistivity than the substrate can provide, additional layers can be added. Alternatively, a non-biological insulator of high dielectric constant can be interposed between two layers of the biologic material for increased resistivity.

A layer of a flexible conducting material may also be added between layers of the biological material to provide electrostatic and electromagnetic shielding. This shielding material may be grounded as necessary.

BRIEF DESCRIPTION OF THE DRAWINGS

Other features of the present invention and many of the attendant advantages will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
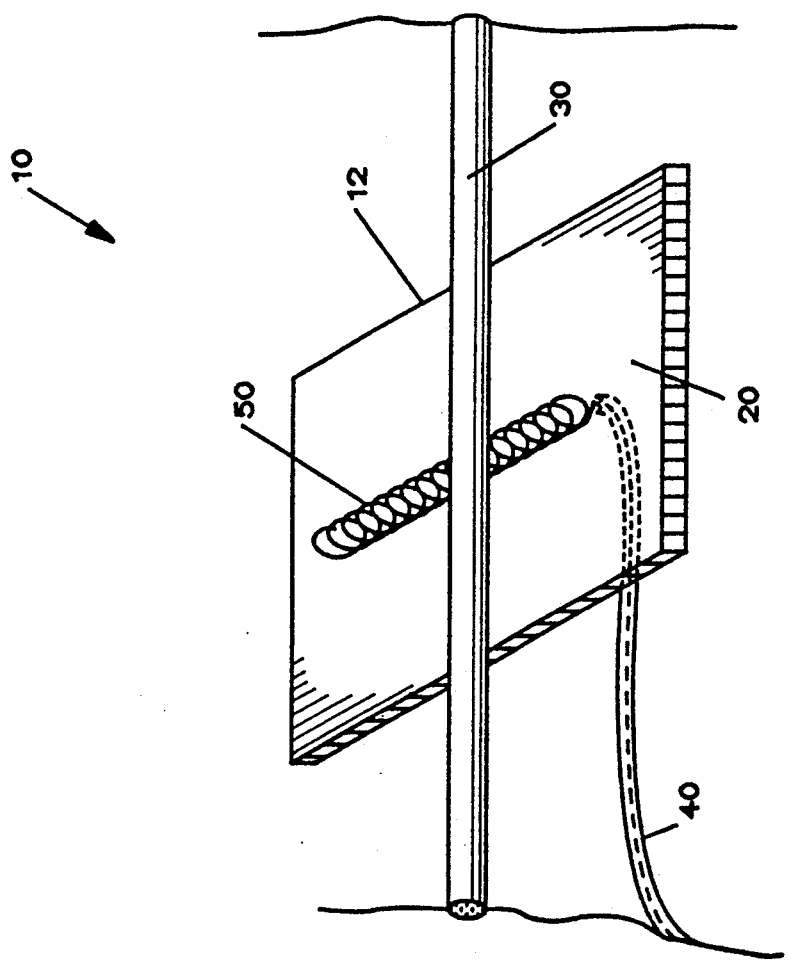
FIG. 1 is a plan view of an electrode of the present invention in position to be wrapped about a nerve.

FIG. 1 is a plan view of an electrode 10 of the present invention placed in proximity to a nerve 30. The electrode 10 has a substrate 12 to which is attached conductor 50 on one side 20. Conductor 50 is configured as a coil or other geometric shape which provides the desired surface area. Conductor 50 is electrically coupled to the distal end of insulated lead 40. The proximal end of lead 40 is coupled to electronic monitoring circuitry which is not shown.

Substrate 12 is of a sufficient size to conveniently wrap about nerve 30 with enough surface area to easily suture into place, without being so large as to be difficult to manage. Substrate 12 may be of a single layer as shown in this embodiment. It is made of a biological material which has been treated to enhance chronic implantability. A preferred material is porcine pericardium, although other biological materials may be used. The biological material is treated with a fixant such as glutaraldehyde.

The insulating properties of the resulting substrate 12 are moderate. Therefore, it may be desirable to use multiple layers of the biological material. A limitation of the use of such auxiliary layers is the desirability of a small and flexible substrate 12.

Figure 2:
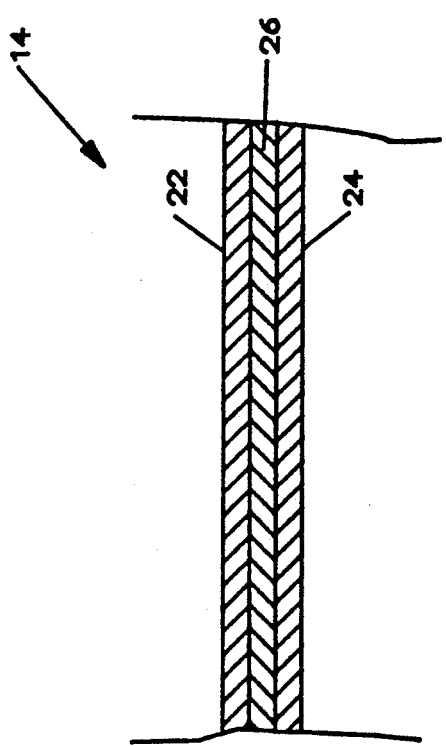
FIG. 2 is a cross sectional cut away view of the layers of an alternate embodiment.

FIG. 2 is a cut away cross sectional view of an alternative embodiment of substrate 14. This embodiment provides greater resistivity with less bulk than can be achieved with multiple layers of biological material. In this embodiment, layers 22 and 24 are of the biological material. They are positioned on the exterior surfaces of substrate 14 to ensure that only the biological material is in contact with nerve 30 and other living body tissue.

Located between layers 22 and 24 is insulating material 26. This may be, without limitation, silicone rubber or other flexible material of high dielectric constant. Because insulating material 26 should be chosen of a chronically implantable material, it need not be covered at the edges by the biological material. However, it is desirable to cover all of insulating material 26 to discourage any unnecessary fibrotic growth.

Figure 3:
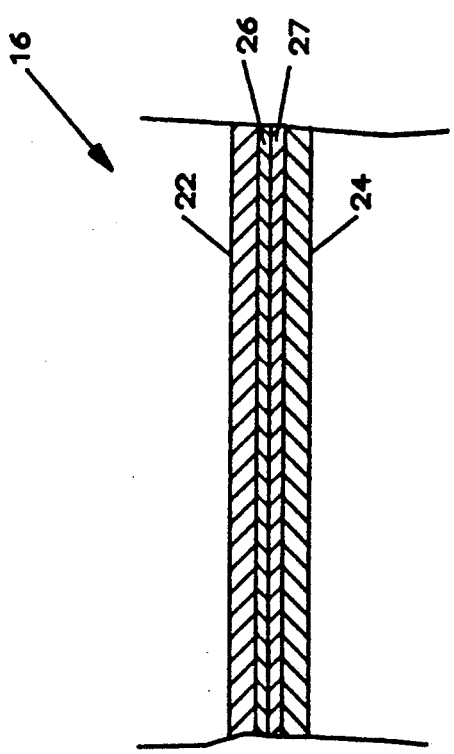
FIG. 3 is a cross sectional cut away view of the layers of a second alternative embodiment; and, FIG. 4 is a plan view of an electrode of the present invention as chronically implanted.

FIG. 3 is a cut away cross sectional view of a second alternative embodiment of substrate 16. Layers 22 and 24 are of the biological material as described in the embodiment of FIG. 2. Similarly, insulating layer 26 consists of the chronically implantable material of high dielectric constant of that embodiment. Layer 27 is a thin flexible metallic layer of a light conductive material. It is preferably of a biocompatible material, such as platinum, as a safety precaution. It also enables the substrate 16 to leave the edges of layer 27 uncovered by any of layers 22, 24, or 26 although it is desirable to do so as explained above.

Layer 27 provides shielding of the electrical interface between nerve 30 and conductor 50. This shielding attenuates electrostatic and electromagnetic noise in the environment. Alternatively, layer 27 may be electrically coupled to ground as is appropriate.

Figure 4:
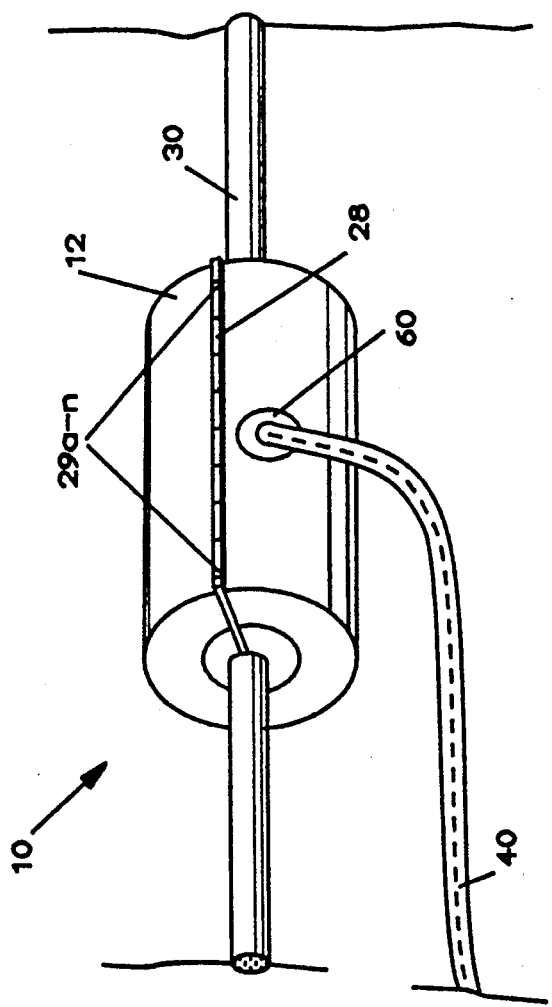

FIG. 4 is a plan view of the electrode 10 as chronically implanted. This particular implantation technique is considered as representative only and should not be construed as limiting of the present invention. Those skilled in the art will readily be able to apply the present invention to other modes of implantation. Substrate 12 is wrapped about nerve 30 as shown. Permanent attachment is accomplished by creating excess flap 28 and applying sutures 29 as shown. The mechanical coupling of the distal end of insulating lead 40 to substrate 12 is sealed using medical adhesive 60.

Having thus described the preferred embodiments of the present invention, those of skill in the art will be readily able to apply the teachings found herein to other embodiments without departing from the scope of the claims hereto attached.

We claim:

1. An electrode comprising:
   a. a substrate of a plurality of layers of a treated biological material wherein at least a first of said plurality of layers is separated from a second of said plurality of layers by a third layer of a material different from said treated biological material;
   b. a conducting surface attached to said substrate; and,
   c. a lead electrically coupled to said conducting surface.

2. An electrode according to claim 1 wherein said third layer comprises a non-biological insulator of high dielectric constant.

3. An electrode according to claim 2 wherein said substrate further comprises a fourth layer of shielding material located between said plurality of layers of said treated biological material.

4. An electrode according to claim 1 wherein said third layer comprises a layer of shielding material.

5. A method of making an electrode comprising:
   a. making a substrate by treating a plurality of layers of a biological material for chronic implantation;
   b. placing a layer of a non-biological material between said plurality of layers of said biological material;
   c. fixedly attaching a conductor to a side of said substrate; and,
   d. electrically coupling a lead to said conductor.

* * * * *